United States Patent [19]

Schneider, Sr.

[11] Patent Number: 4,539,977
[45] Date of Patent: Sep. 10, 1985

[54] THERAPEUTIC SUPPORT MEANS

[76] Inventor: Paul E. Schneider, Sr., 300 N. Main St., Woodsfield, Ohio 43793

[21] Appl. No.: 468,972

[22] Filed: Feb. 23, 1983

Related U.S. Application Data

[63] Continuation of Ser. No. 212,397, Dec. 3, 1980, abandoned.

[51] Int. Cl.³ .............................................. A61F 5/00
[52] U.S. Cl. ..................................... 128/68; 297/439; 272/111
[58] Field of Search ............ 272/111, 1 R; 128/25 B, 128/68, 78, 57; 297/439

[56] References Cited

U.S. PATENT DOCUMENTS

| | | | |
|---|---|---|---|
| 1,407,642 | 2/1922 | Day et al. | 272/111 |
| 2,080,208 | 5/1937 | Illch | 128/25 B |
| 2,082,829 | 6/1938 | Gerlofson | 128/25 B |
| 2,121,251 | 6/1938 | Koschwitz | 128/25 B |
| 2,638,089 | 5/1953 | Murphy | 128/25 B |
| 3,589,716 | 6/1971 | Footlik | 272/111 |
| 4,105,201 | 8/1978 | Ecuyer | 272/111 |

FOREIGN PATENT DOCUMENTS 1553538 12/1978 France ................. 272/111

Primary Examiner—Richard C. Pinkham
Assistant Examiner—T. Brown
Attorney, Agent, or Firm—Reed, Smith, Shaw & McClay

[57] ABSTRACT

A therapeutic support for supporting the foot of an individual while seated to provide therapeutic relief to the individual's lower back. The support comprises a pair of spaced apart vertical end plates and a tubular cross member joining said end plates. The tubular cross member is eccentrically mounted to the respective end means to provide a number of different elevations for positioning the foot or feet.

1 Claim, 2 Drawing Figures

THERAPEUTIC SUPPORT MEANS

This application is a continuation of U.S. Ser. No. 06/212,397, filed 12/03/80 (ABANDONED).

FIELD OF THE INVENTION

The invention relates to a support means for providing therapeutic relief to an individual's lower back, and, in particular, to an elevated support for an individual's feet which provides relief to the lower back.

BACKGROUND OF THE INVENTION

There are a number of prior art devices which are addressed to supporting or exercising one's back, for example, U.S. Pat. Nos. 4,207,635 and 4,204,676. Both of the devices disclosed in such patents are designed to provide relief to the back, however, they do not provide such relief through the direct intervention of the positioning or elevation of the leg or foot.

While it has been generally known to use stools or other leg supporting devices, e.g., U.S. Pat. Nos. 3,696,458; 3,577,936 and 3,696,826 to provide relief to the legs, such devices have not been known to provide relief to the lower back.

Accordingly, it is an object of the present invention to provide a therapeutic support which will provide relief to the lower back by providing a variety of supported elevations which a seated individual can rest the leg or foot. It is a further object of the invention to provide a support means which is not only rigid, but one which is simple to make. Of even greater importance, it is an object of the invention to provide a support means which is light in weight so that a person experiencing lower back problems can lift, transport or adjust it.

SUMMARY OF THE INVENTION

Generally, the present invention comprises a pair of spaced apart vertical end means. Each end means is preferably square in configuration. A support position member, preferably tubular in configuration, is positioned between the two end means. The support member is eccentrically mounted to the end means.

It has been found that elevations of only a few inches to support an individual's leg will afford therapeutic relief to the lower back. Accordingly, it has been found desirable to make the end means about seven to ten inches square. The spanning support member is eccentrically mounted so that rotation of the entire support means will provide at least four different elevations. Other configurations of the end means, such as octagonal, will provide addition elevation adjustments.

The present invention is relatively easy and inexpensive to manufacture, because there are no moving parts. The design provides a rigid support while at the same time facilitating elevation adjustments. Other advantages of the invention will become apparent from a perusal of the following detailed description of a presently preferred embodiment taken in conjunction with the accompanying drawings.

PREFERRED EMBODIMENT

Figure 1:
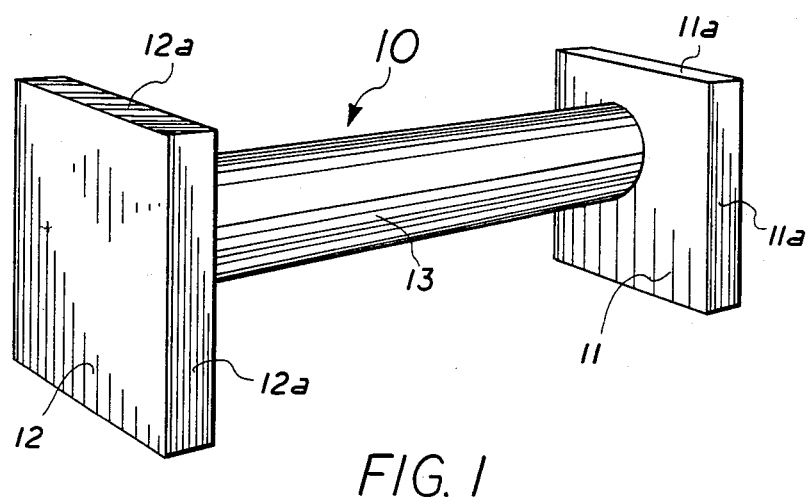
FIG. 1 is a perspective view of the support means of the present invention.

Referring to the drawings, support means 10 comprises a pair of end means 11 and 12. As shown, end means 11 and 12 have four sides 11a and 12a, respectively, and are desirably of the same length, for example 7" to 10" and include a skid resistance surface. Preferably, the end means are square in shape; however, each of said ends may be triangular, hexagonal, octagonal or the like in shape. It is not desirable, however, to make the respective sides 11a or 12a a continuum such that the associated end means are substantially circular in shape, because such shape would permit the support means 10 to roll. End means 11 and 12 may be made from wood, aluminum, a rigid plastic material or other rigid, light weight material.

Figure 2:
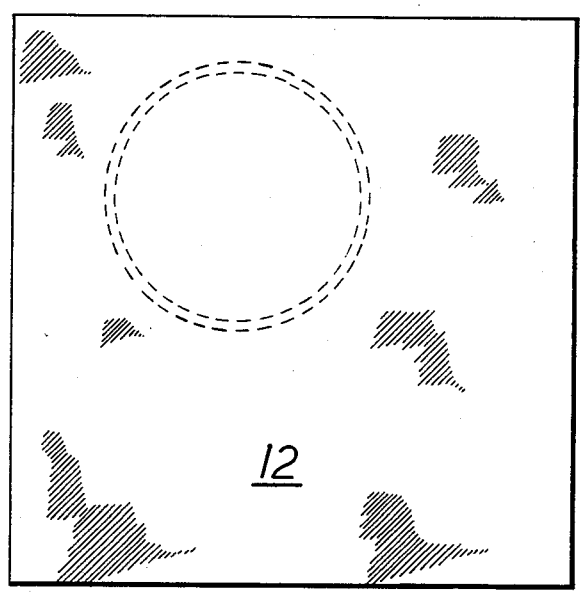
FIG. 2 is an elevation of the end means shown in FIG. 1.

The end means 11 and 12 are connected by support member 13. As shown in FIG. 2, support member 13 is preferably cylindrical and tubular. While it is not necessary that member 13 be cylindrical, it is highly desirable to make it tubular to minimize the weight of support means 10. Support member 13 is eccentrically mounted to end means 11 and 12. Mounting may be achieved by adhesives or more desirably by providing annular recesses in each end means adapted to engagingly receiver support member 13.

In a presently preferred embodiment, tubular support member 13 is 3" to 4" in diameter and 15" to 20" in length. The invention in its preferred configuration and size provides therapeutic relief to the lower back to a seated individual resting their foot on support member 13. By rotating support means 10 so that it rests on different sides 11a and 12a, the elevation of support member 13 can be varied. Surprisingly, while these variations in elevation are not substantial, they provide the necessary relief to the lower back for long periods of time.

While a presently preferred embodiment has been shown and described in particularity, it may be otherwise embodied within the scope of the appended claims.

What is claimed is:

1. A means for therapeutic relief of the lower back pain comprising:
   (a) a pair of spaced apart end means, each of said end means having at least three peripheral substantially planar surfaces, each of said surfaces oriented in the same plane as a corresponding surface of the opposite end means to provide a plurality of stable base surfaces for said therapeutic support means, and each of said means is a square whereby four substantially horizontal foot-support surfaces of varying heights are provided; and
   (b) a support member having a cross-sectional area substantially less than said end means and joining said end means together, said support member secured horizontally between said end means but offset relative to the centerpoint thereof in a manner whereby a plurality of substantially horizontal foot-support surfaces of varying heights are provided, each in response to rotary selection of one of said plurality of stable base surfaces, and further wherein said support member is a cylindrical tube.

* * * * *